United States Patent
Bibulić et al.

(10) Patent No.: US 12,421,214 B2
(45) Date of Patent: Sep. 23, 2025

(54) SOLID STATE FORMS OF APROCITENTAN AND PROCESS FOR PREPARATION THEREOF

(71) Applicant: ASSIA CHEMICAL INDUSTRIES LTD., Tel Aviv (IL)

(72) Inventors: Petar Bibulić, Zagreb (HR); Sanja Matečić Mušanić, Zagreb (HR)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 499 days.

(21) Appl. No.: 17/922,007

(22) PCT Filed: May 21, 2021

(86) PCT No.: PCT/US2021/033525
§ 371 (c)(1),
(2) Date: Oct. 28, 2022

(87) PCT Pub. No.: WO2021/237004
PCT Pub. Date: Nov. 25, 2021

(65) Prior Publication Data
US 2023/0167090 A1  Jun. 1, 2023

Related U.S. Application Data

(60) Provisional application No. 63/028,159, filed on May 21, 2020.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .................... C07D 403/12; C07B 2200/13
See application file for complete search history.

(56) References Cited

U.S. PATENT DOCUMENTS

| | | | |
|---|---|---|---|
| 8,324,232 B2 | 12/2012 | Bolli | |
| 11,680,058 B2 * | 6/2023 | Bolli | A61K 45/06 514/269 |
| 11,787,782 B2 * | 10/2023 | Bellet | A61K 45/06 514/222.5 |
| 2020/0002317 A1 | 1/2020 | Bolli | |

FOREIGN PATENT DOCUMENTS

| | | |
|---|---|---|
| CN | 112679441 A | 4/2021 |
| EP | 2907811 A1 | 8/2015 |

OTHER PUBLICATIONS

Mino R Caira, "Crystalline Polymorphism of Organic Compounds", Jan. 1, 1998, vol. 198, p. 163-208, XP008166276.
International Search Report and Written Opinion of the International Searching Authority issued in corresponding application PCT/US2021/033525 mailed Oct. 14, 2021 (17 pages).

* cited by examiner

*Primary Examiner* — Kamal A Saeed
(74) *Attorney, Agent, or Firm* — CARTER, DELUCA & FARRELL LLP

(57) ABSTRACT

The present disclosure encompasses novel solid state forms of Aprocitentan, Aprocitentan salts and Aprocitentan co-crystals, processes for preparation thereof, and pharmaceutical compositions thereof.

15 Claims, 19 Drawing Sheets

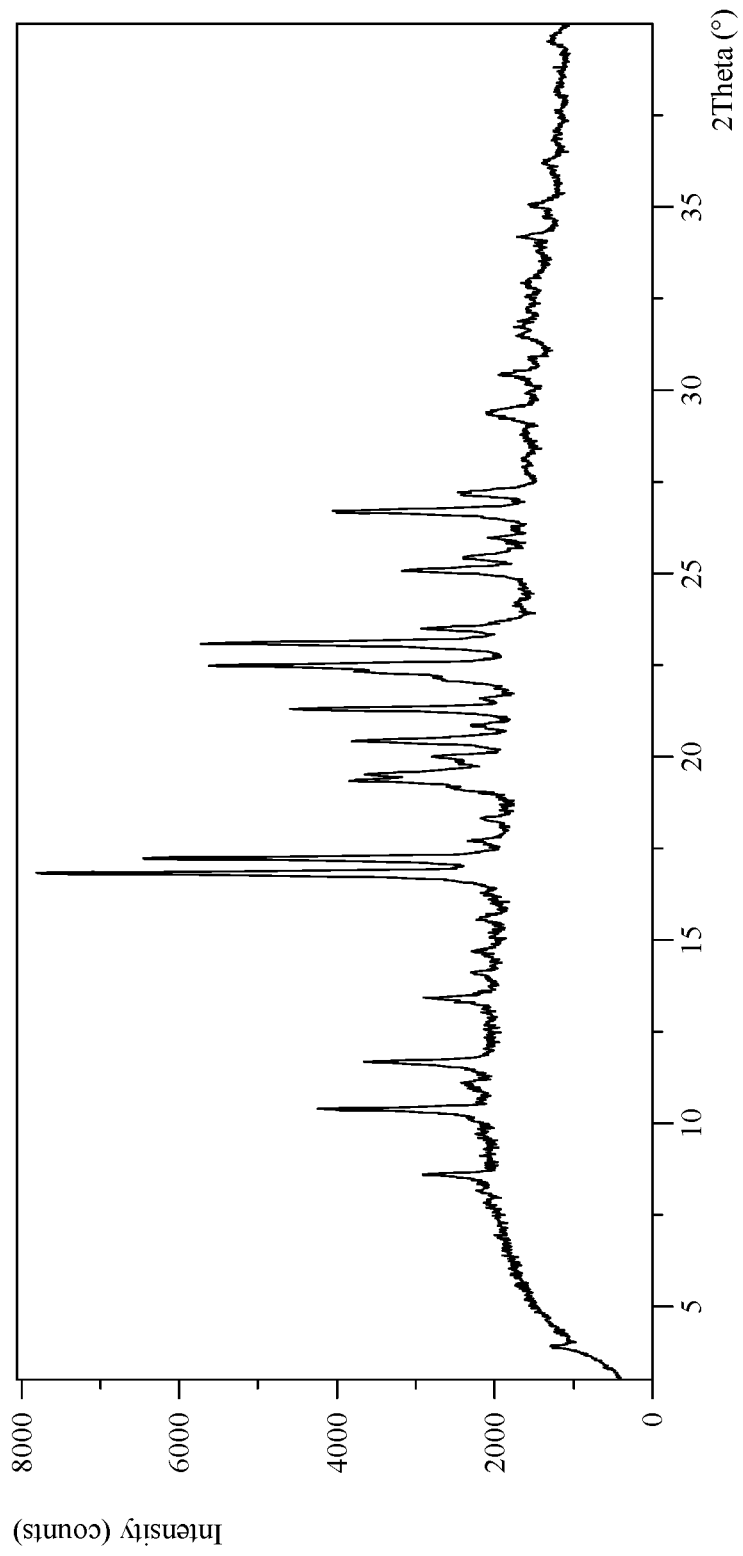
Figure 1. XRPD pattern of crystalline Aprocitentan:piperazine Form P1

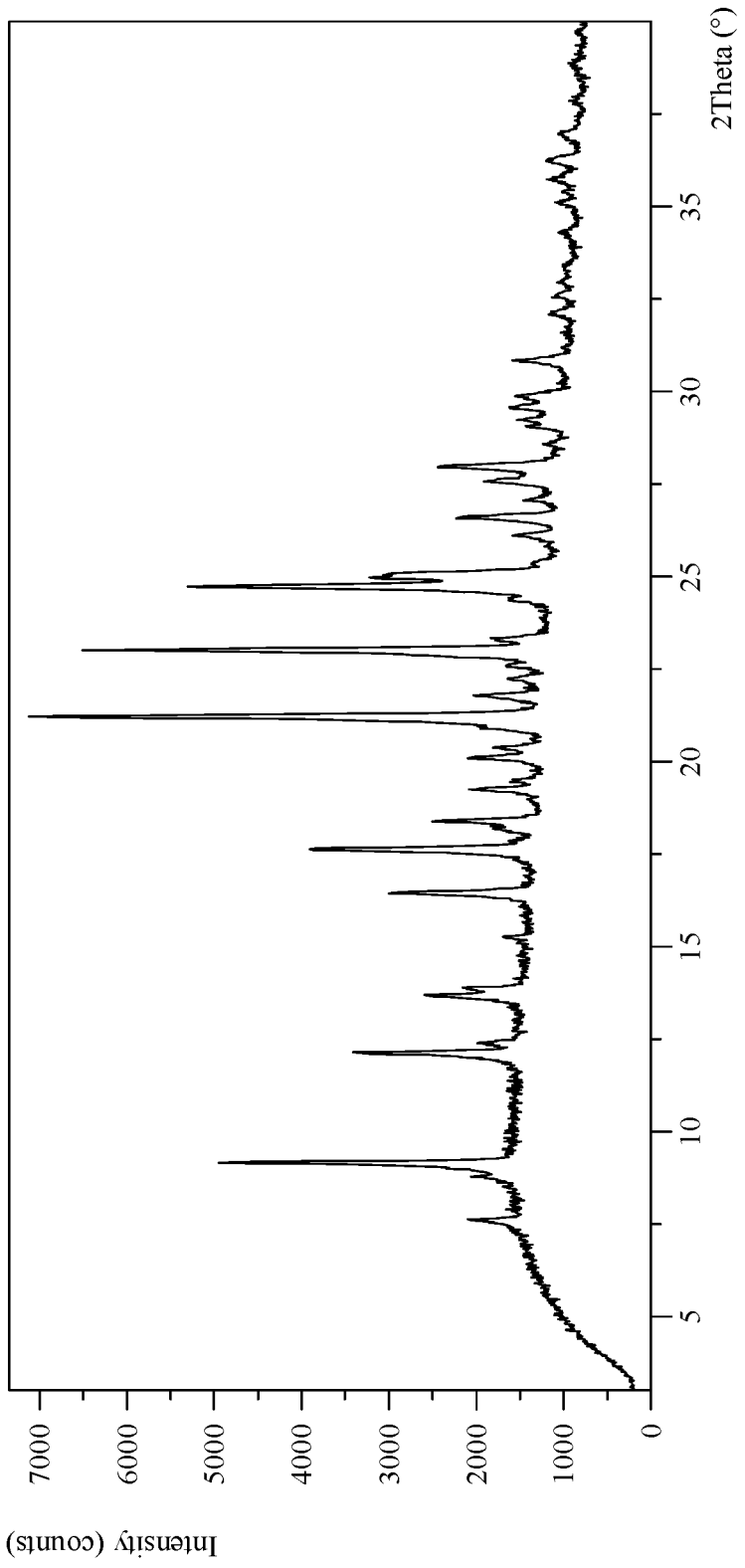

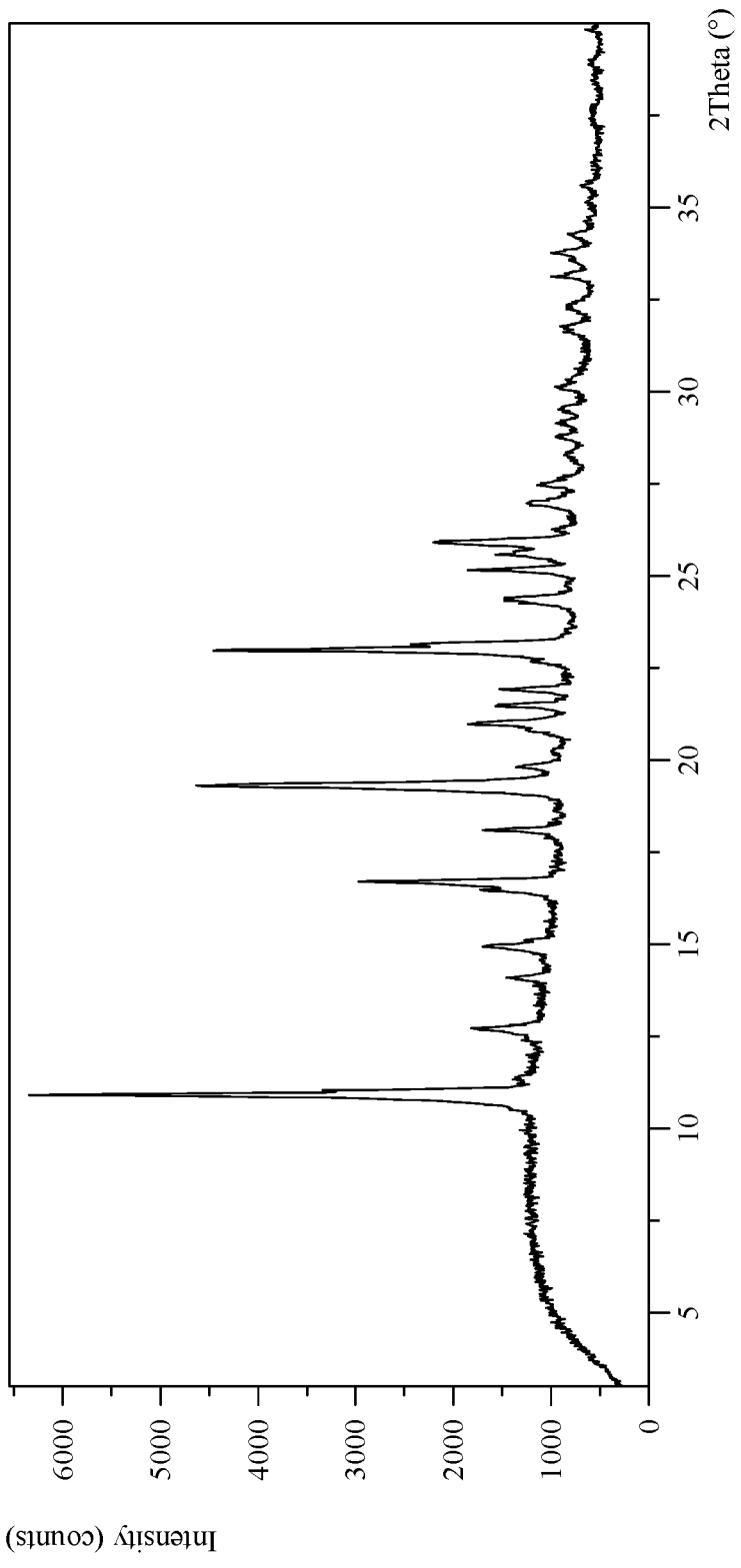

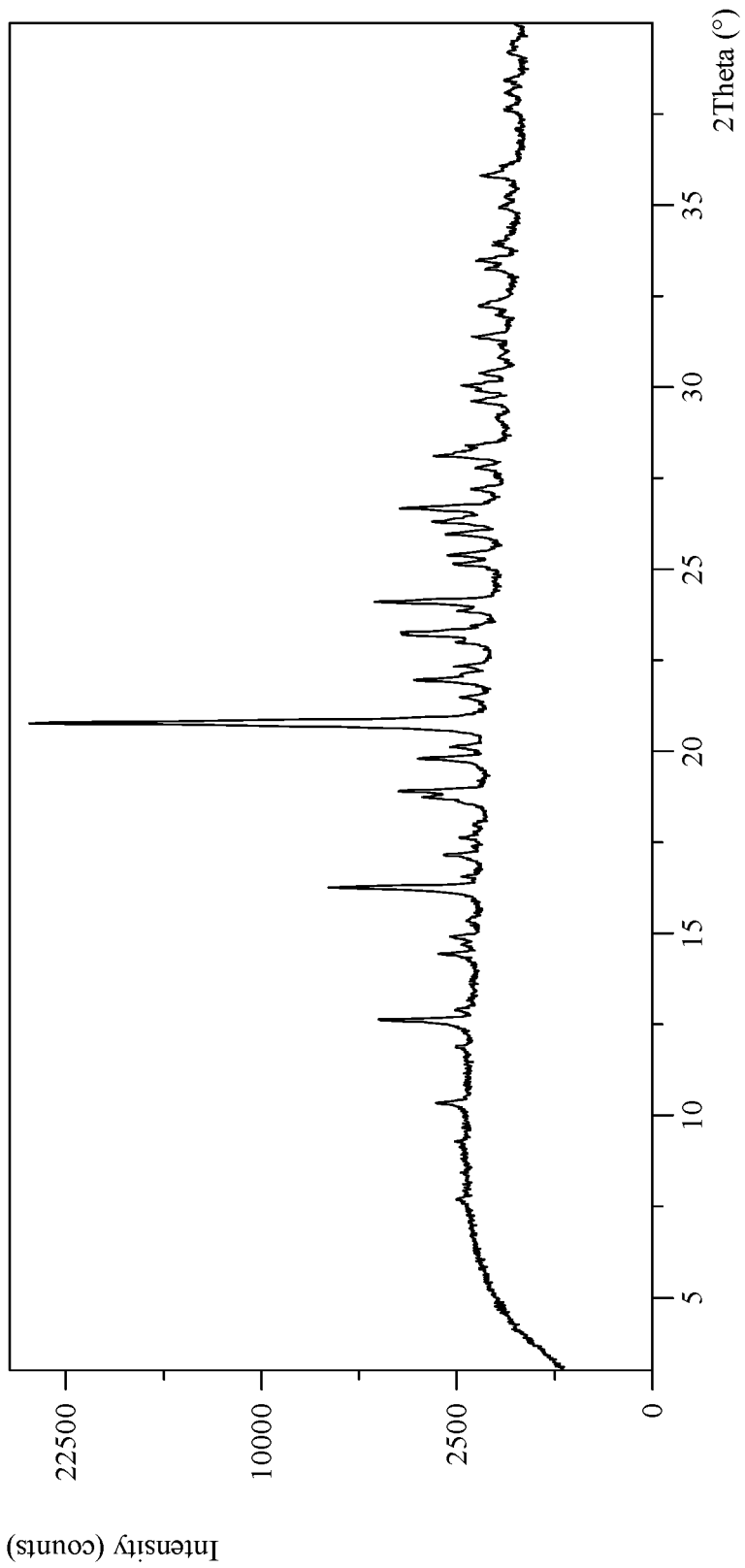
Figure 4. XRPD pattern of crystalline Aprocitentan Form T9

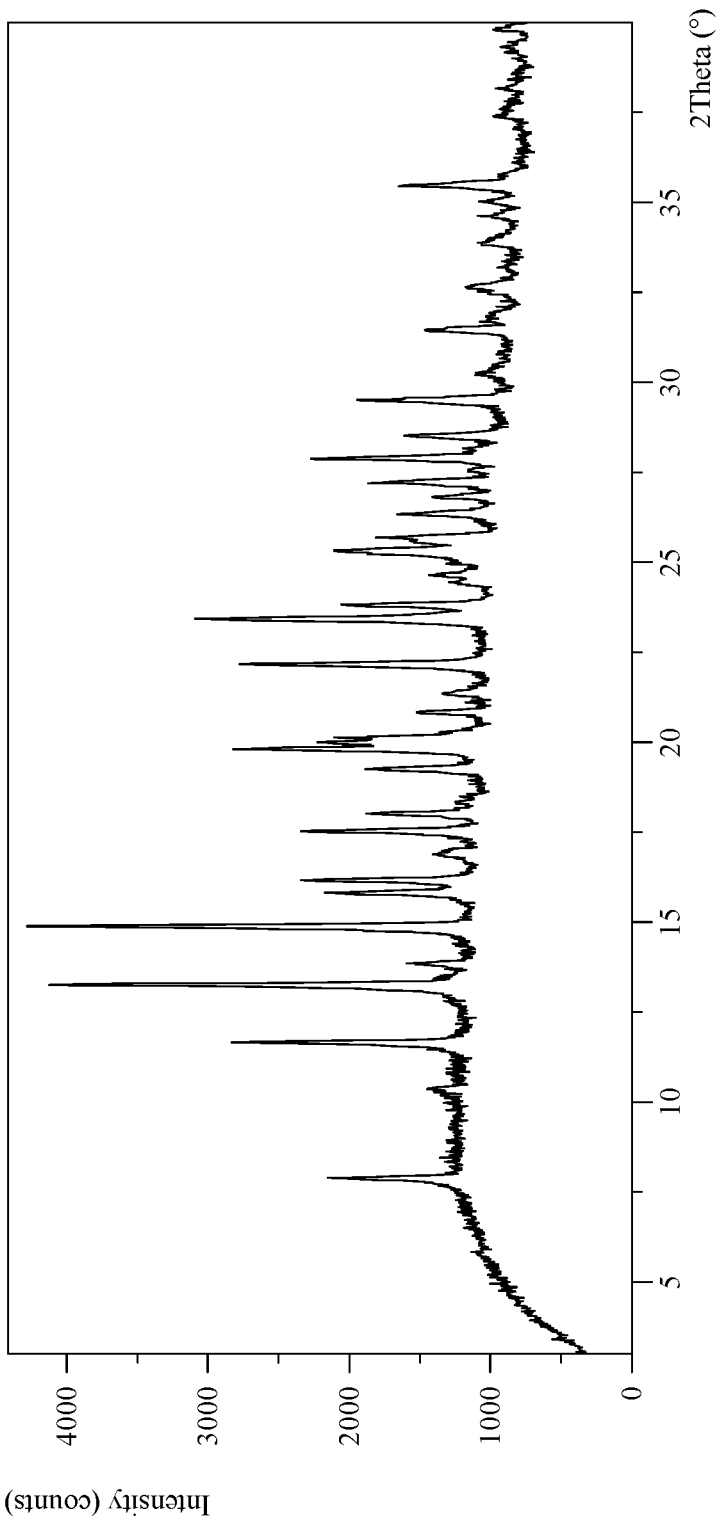

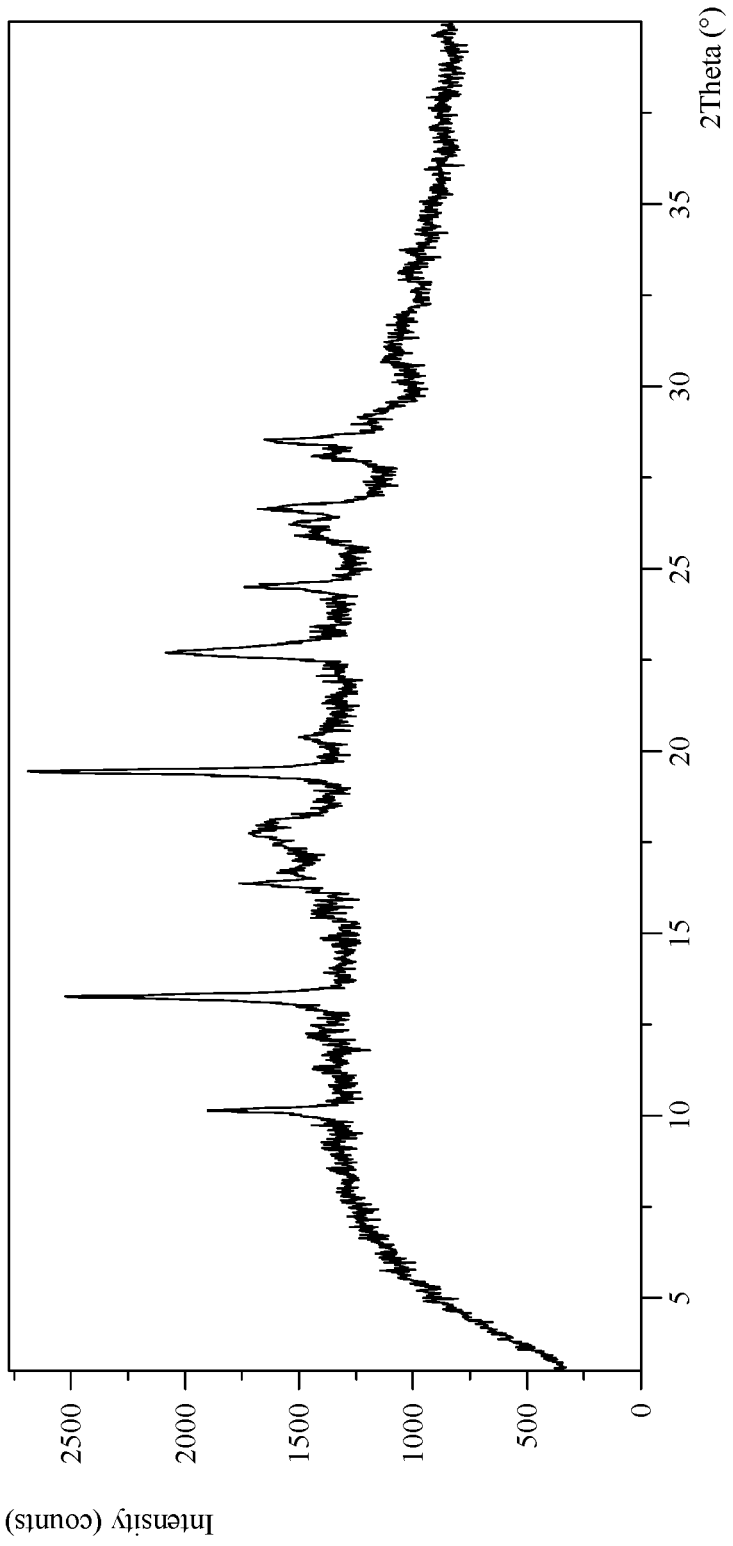
Figure 6. XRPD pattern of crystalline Aprocitentan Form T12

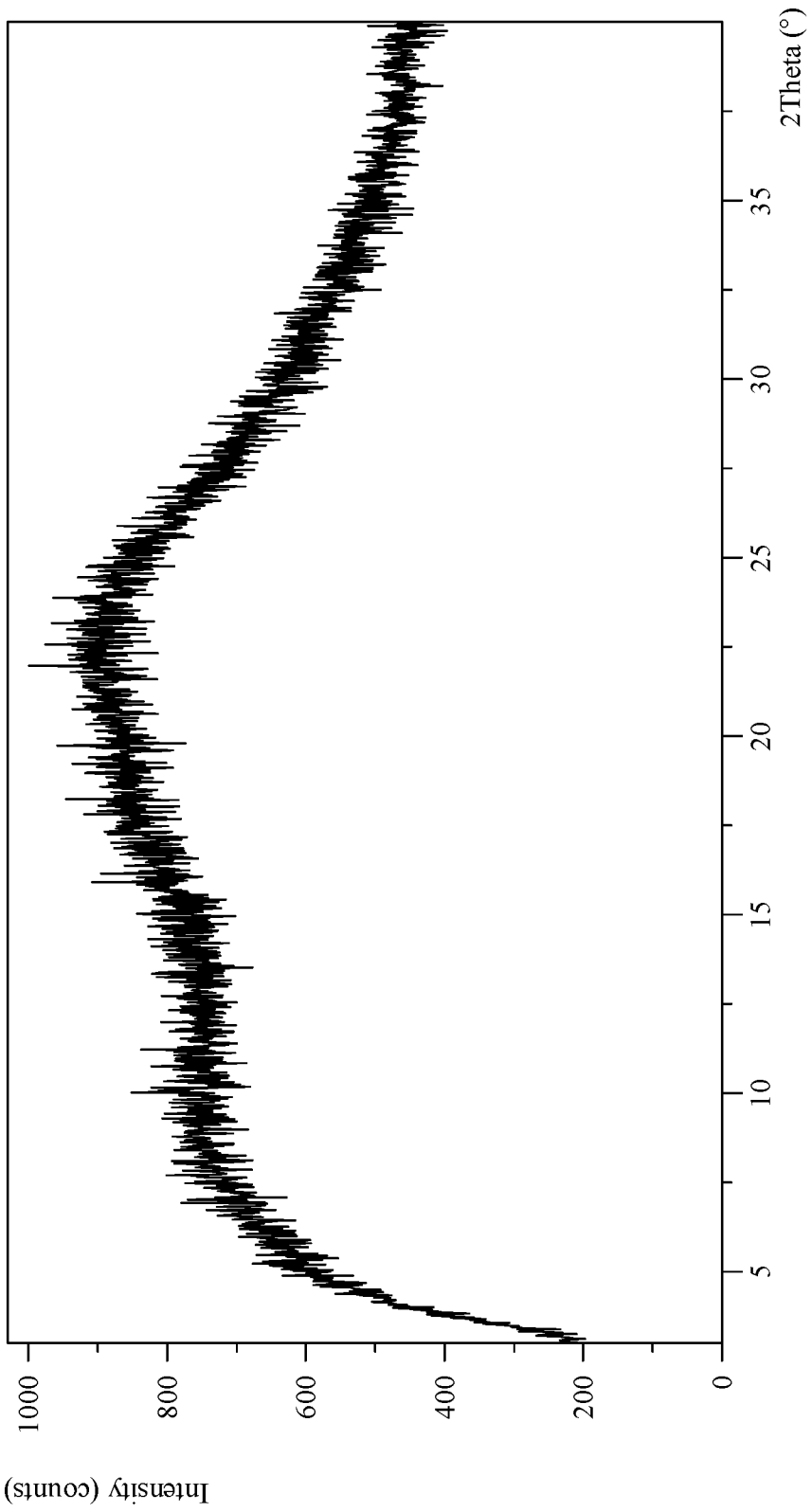
Figure 7. XRPD pattern of amorphous Aprocitentan

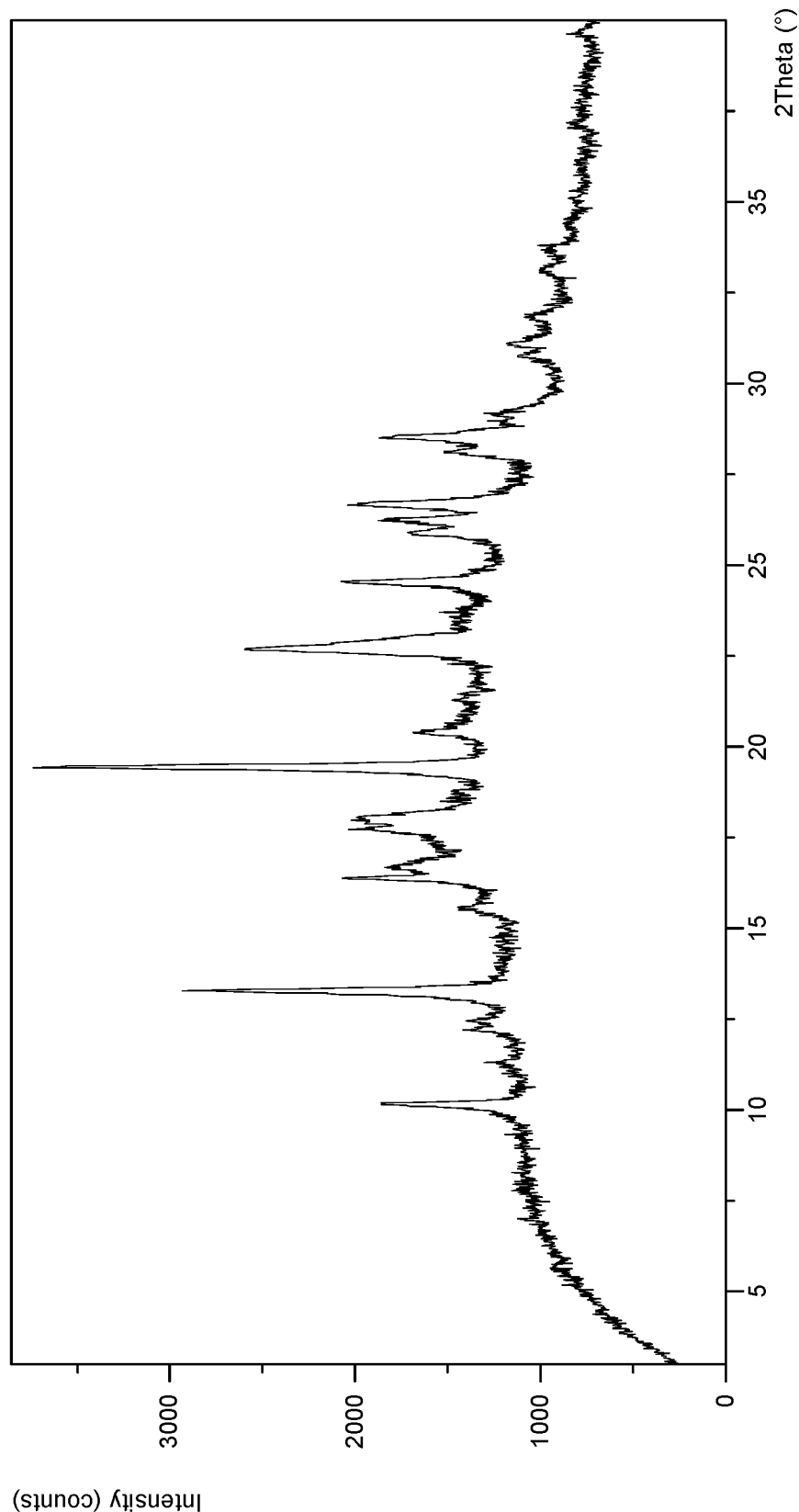
Figure 8. XRPD pattern of crystalline Aprocitentan Form T12

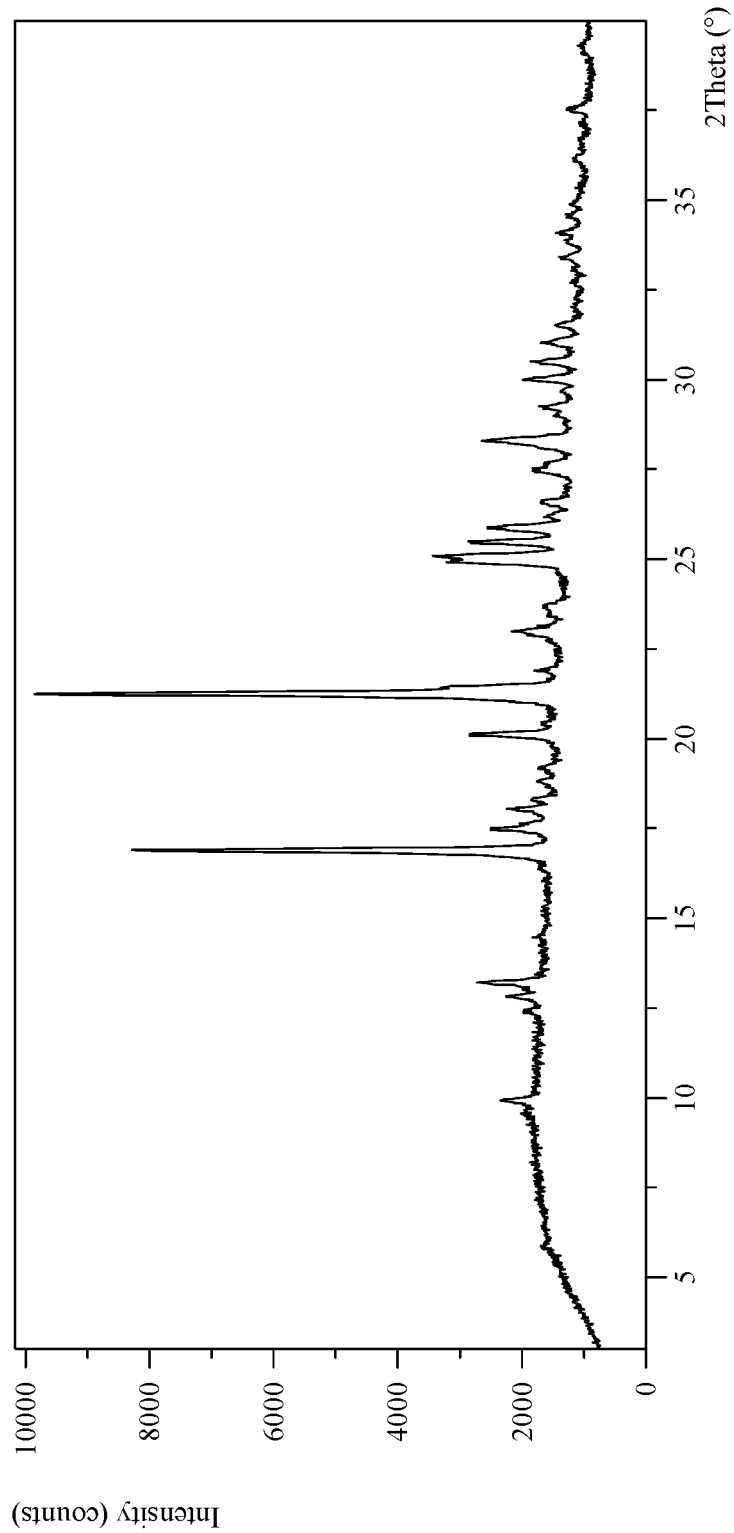
Figure 9. XRPD pattern of crystalline Aprocitentan piperazine Form P2

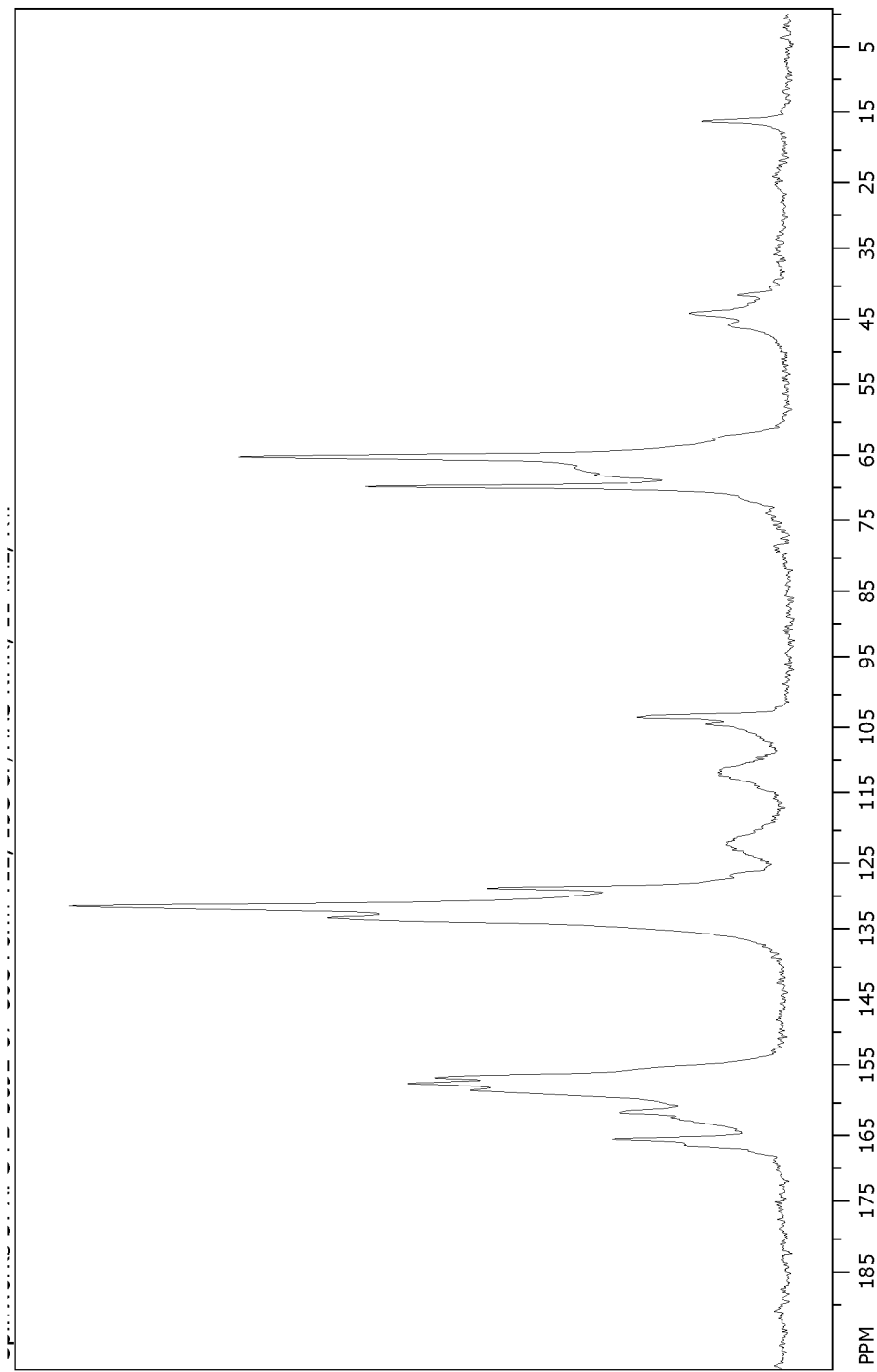
Figure 10: ¹³C-NMR spectrum of crystalline Aprocitentan Form T12

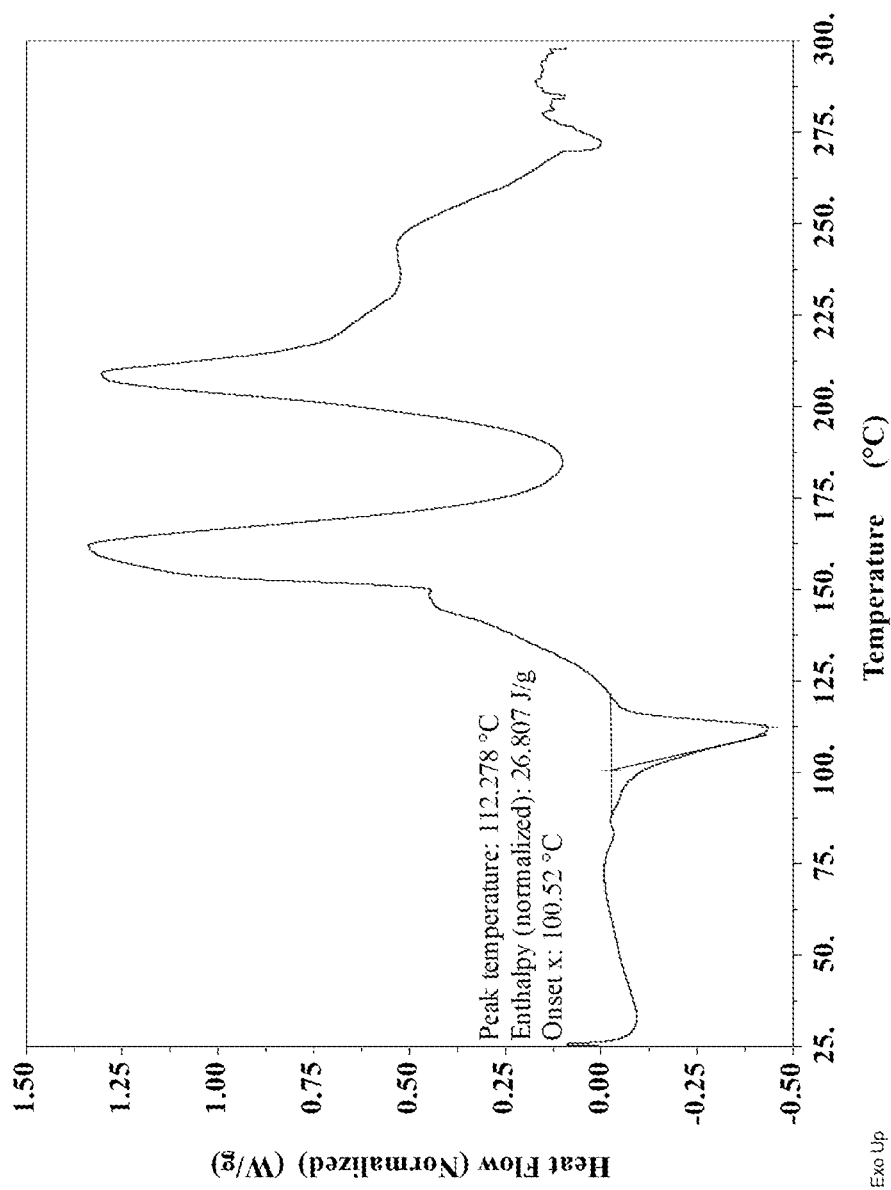
Figure 11: DSC thermogram of crystalline Aprocitentan Form T12

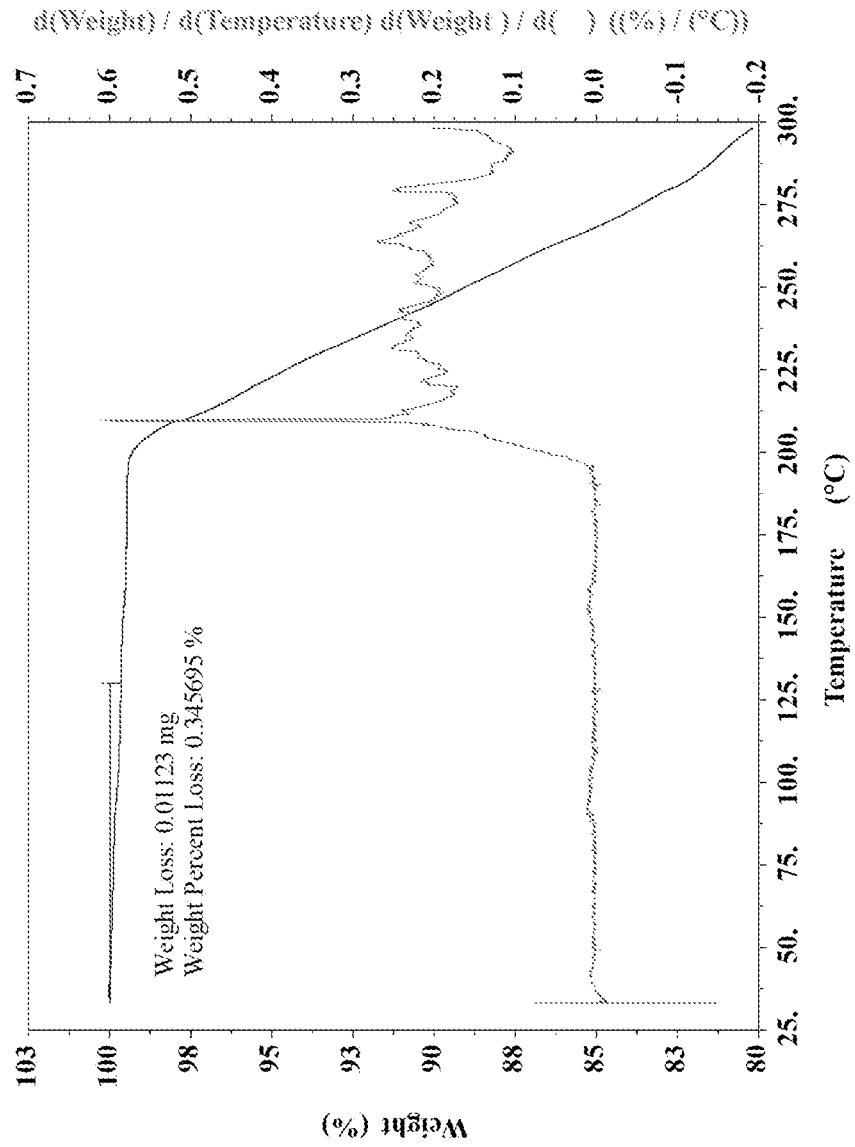
Figure 12: TGA thermogram of crystalline Aprocitentan Form T12

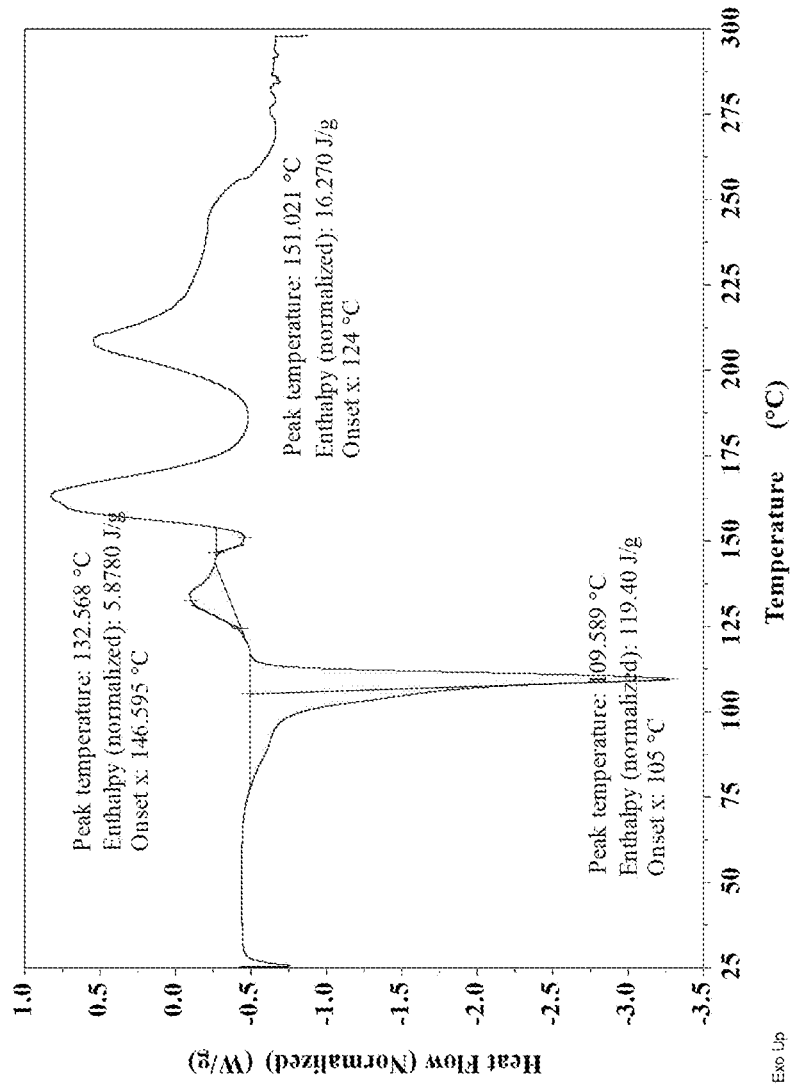

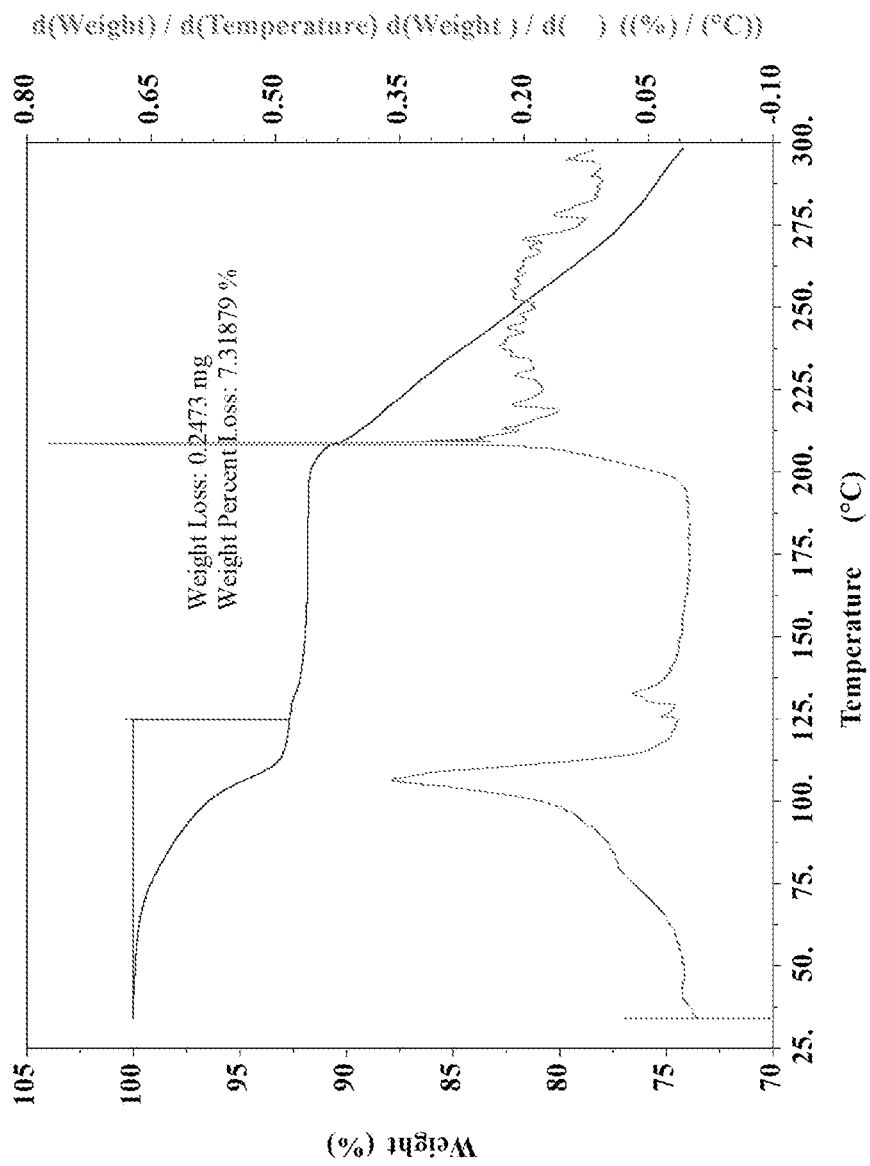
Figure 14: TGA thermogram of crystalline Aprocitentan Form T10

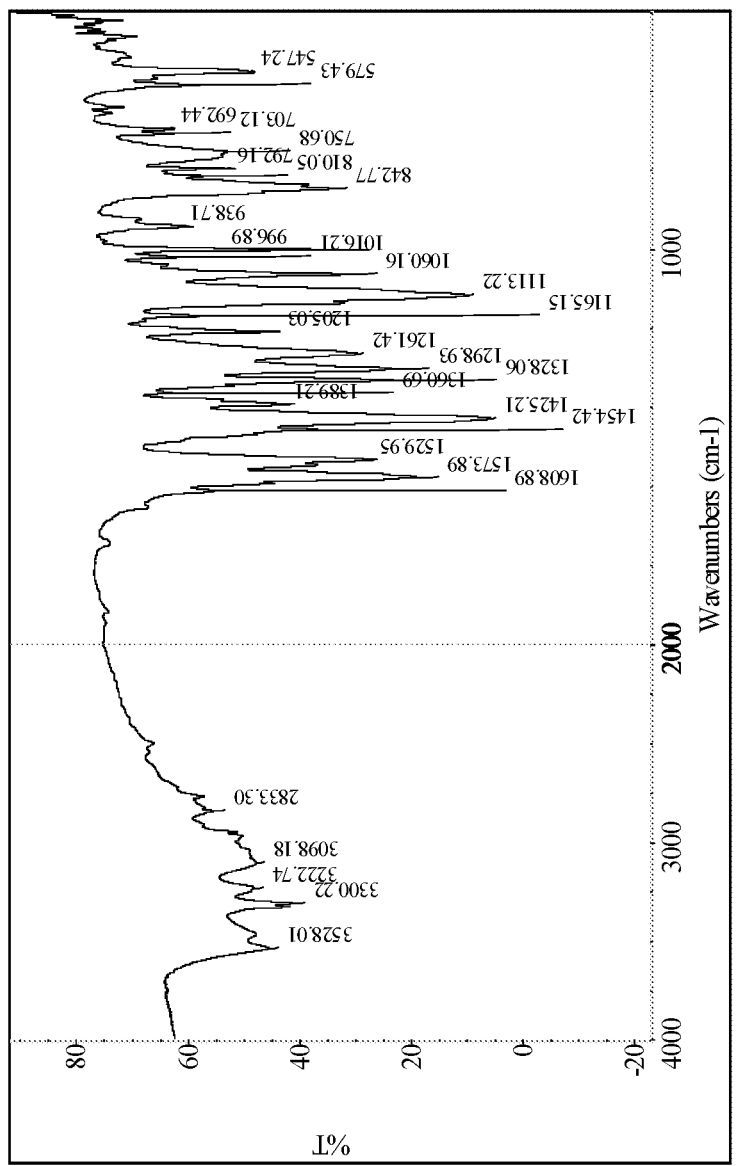

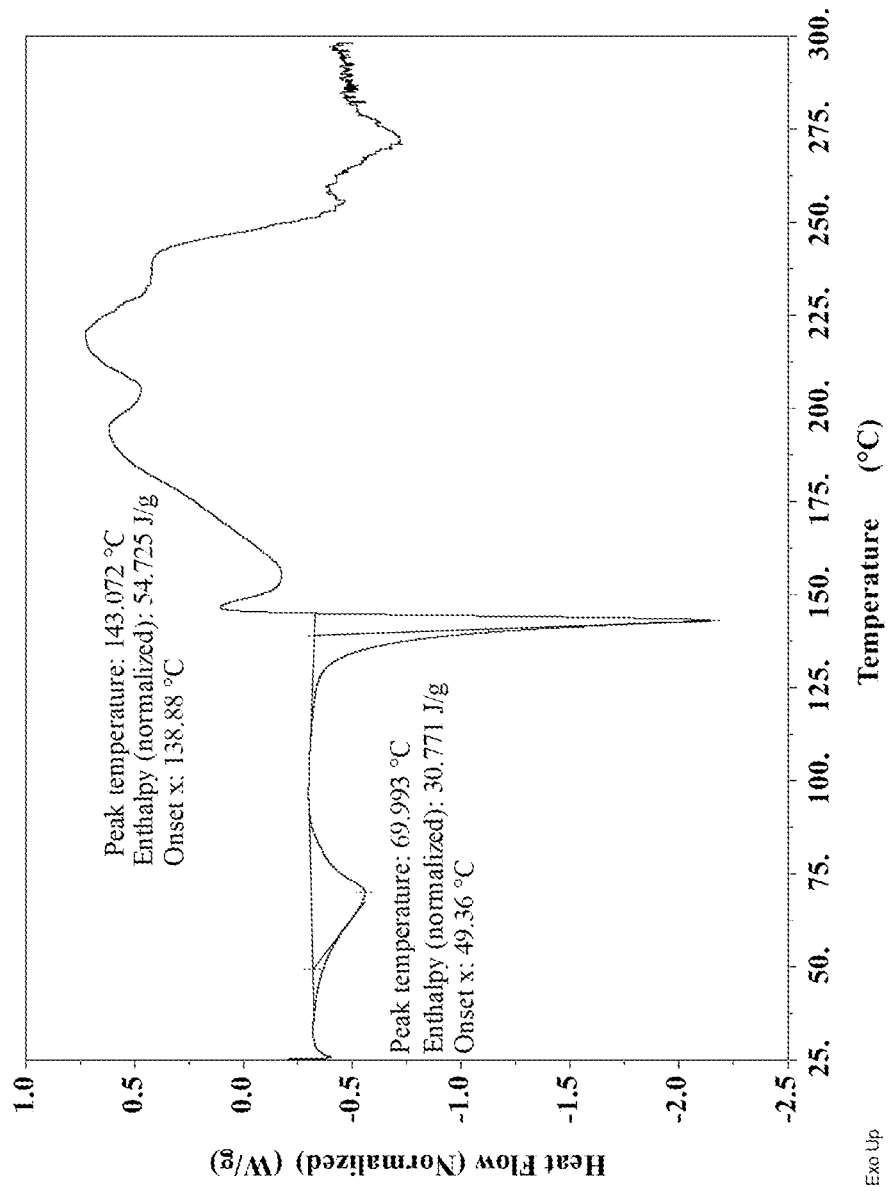
Figure 16: DSC thermogram of Aprocitentan : piperazine Form P1

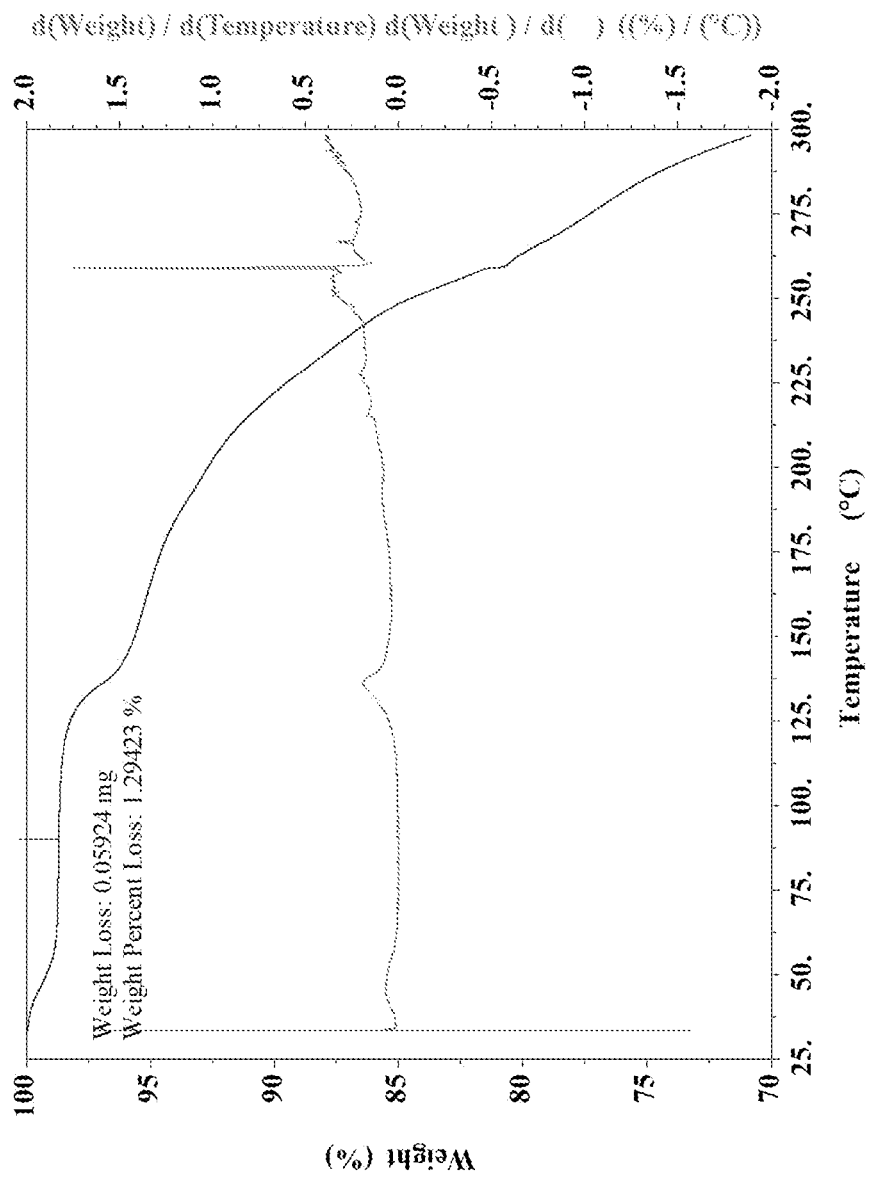

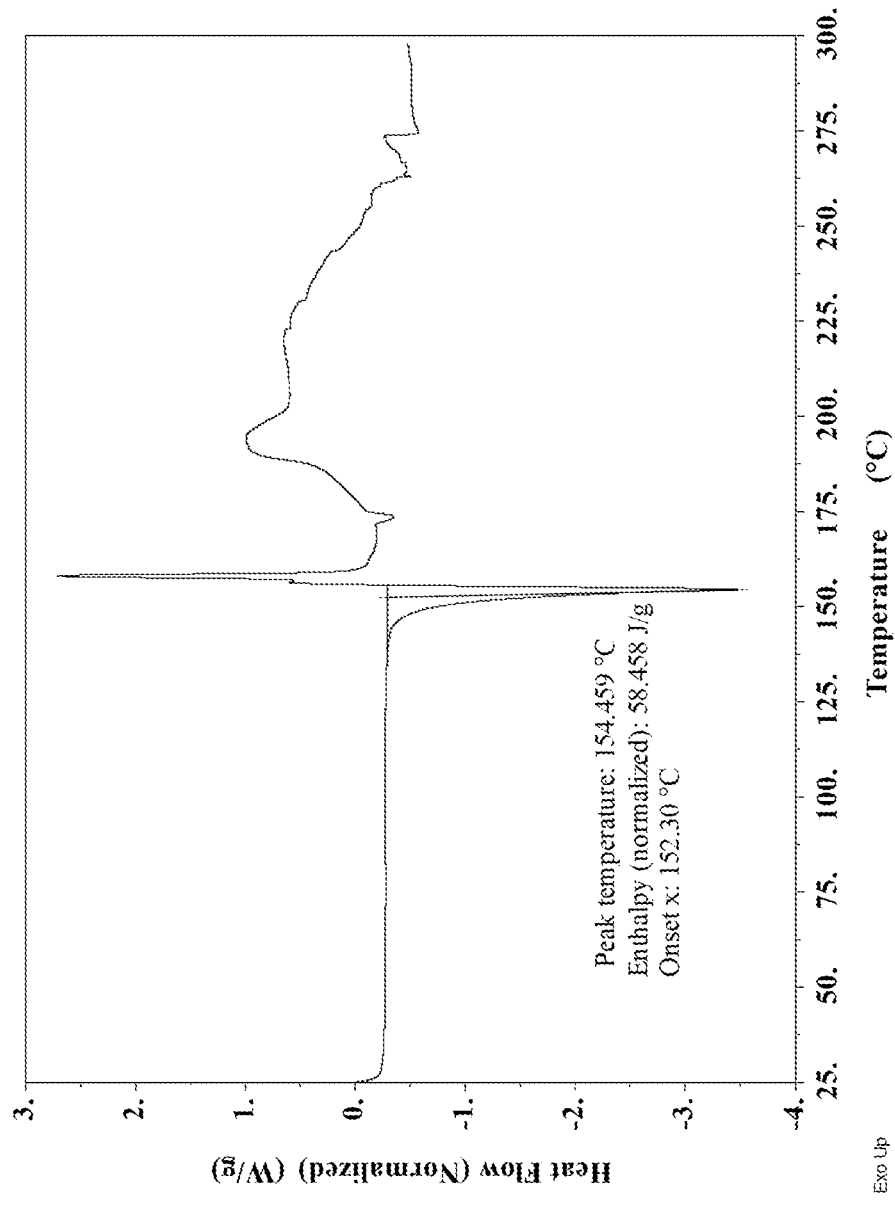
Figure 18: DSC thermogram of Aprocitentan : piperazine Form P2

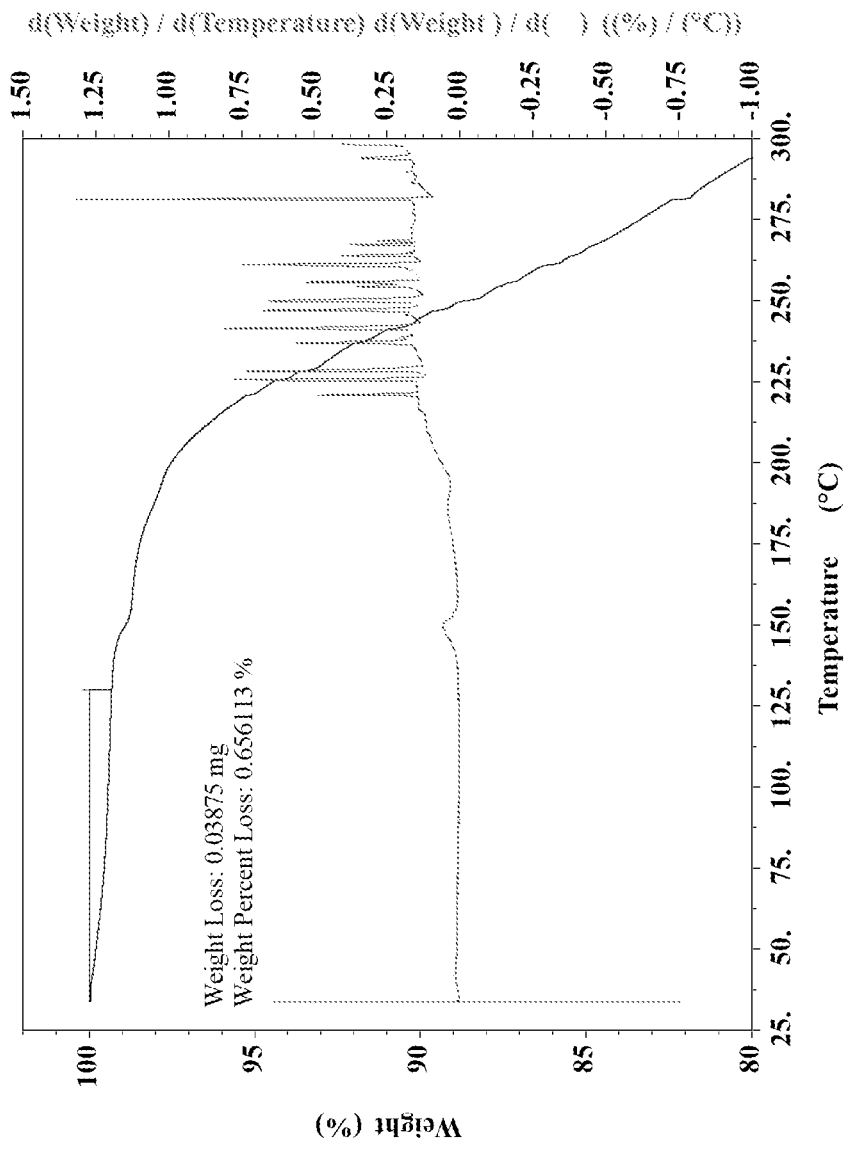
Figure 19: TGA thermogram of Aprocitentan : piperazine Form P2

SOLID STATE FORMS OF APROCITENTAN AND PROCESS FOR PREPARATION THEREOF

CROSS REFERENCE TO RELATED APPLICATIONS

This application is a National Stage of, and claims priority to and the benefit of, International Patent Application No. PCT/US2021/033525, filed May 21, 2021, which, in turn, claims the benefit of and priority to, U.S. Provisional Application No. 63/028,159, filed May 21, 2020, the entire disclosures of each of which are incorporated by reference herein.

FIELD OF THE DISCLOSURE

The present disclosure encompasses solid state forms of Aprocitentan, Aprocitentan salts and Aprocitentan co-crystals, in embodiments crystalline forms of Aprocitentan, Aprocitentan:piperazine, Aprocitentan:methanesulfonic acid, Aprocitentan:ethanesulfonic acid, processes for preparation thereof, and pharmaceutical compositions thereof.

BACKGROUND OF THE DISCLOSURE

Aprocitentan, {5-(4-bromo-phenyl)-6-[2-(5-bromo-pyrimidin-2-yloxy)-ethoxy]-pyrimidin-4-yl}-sulfamide, has the following chemical structure:

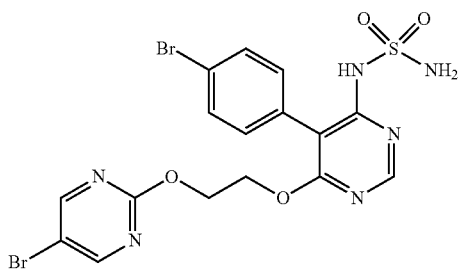 [SMILES: NS(=O)(=O)Nc1ncnc(OCCOc2ncc(Br)cn2)c1-c1ccc(Br)cc1]

Aprocitentan is an endothelin receptor antagonist (ERA), and it is developed for the treatment of hypertension by Idorsia Ltd.

The compound is described in U.S. Pat. No. 8,324,232. Different crystalline Forms of Aprocitentan are disclosed in U.S. Patent Publication No. 2020/0002317.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms and co-crystals) of Aprocitentan.

SUMMARY OF THE DISCLOSURE

The present disclosure provides crystalline polymorphs of Aprocitentan, Aprocitentan:piperazine, Aprocitentan:methanesulfonic acid, and Aprocitentan:ethanesulfonic acid, processes for preparation thereof, and pharmaceutical compositions thereof. These crystalline polymorphs can be used to prepare other solid state forms of Aprocitentan, Aprocitentan salts and their solid state forms, or other co-crystals of Aprocitentan.

The present disclosure also provides uses of the said solid state forms of Aprocitentan, Aprocitentan:piperazine, Aprocitentan:methanesulfonic acid, or Aprocitentan:ethanesulfonic acid in the preparation of other solid state forms of Aprocitentan or salts or co-crystals thereof.

The present disclosure provides crystalline polymorphs of Aprocitentan, Aprocitentan:piperazine, Aprocitentan:methanesulfonic acid, or Aprocitentan:ethanesulfonic acid for use in medicine, including for the treatment of hypertension.

The present disclosure also encompasses the use of crystalline polymorphs of Aprocitentan, Aprocitentan:piperazine, Aprocitentan:methanesulfonic acid, or Aprocitentan:ethanesulfonic acid of the present disclosure for the preparation of pharmaceutical compositions and/or formulations.

In another aspect, the present disclosure provides pharmaceutical compositions comprising crystalline polymorphs of Aprocitentan, Aprocitentan:piperazine, Aprocitentan:methanesulfonic acid, or Aprocitentan:ethanesulfonic acid according to the present disclosure.

The present disclosure includes processes for preparing the above mentioned pharmaceutical compositions. The processes include combining any one or a combination of the crystalline polymorphs of Aprocitentan, Aprocitentan:piperazine, Aprocitentan:methanesulfonic acid, or Aprocitentan:ethanesulfonic acid with at least one pharmaceutically acceptable excipient.

The crystalline polymorph of Aprocitentan, Aprocitentan:piperazine, Aprocitentan:methanesulfonic acid, or Aprocitentan:ethanesulfonic acid as defined herein and the pharmaceutical compositions or formulations of the crystalline polymorph of Aprocitentan, Aprocitentan:piperazine, Aprocitentan:methanesulfonic acid, or Aprocitentan:ethanesulfonic acid may be used as medicaments, such as for the treatment of hypertension.

The present disclosure also provides methods of treating hypertension, by administering a therapeutically effective amount of any one or a combination of the crystalline polymorphs of Aprocitentan, Aprocitentan:piperazine, Aprocitentan:methanesulfonic acid, or Aprocitentan:ethanesulfonic acid of the present disclosure, or at least one of the above pharmaceutical compositions, to a subject suffering from hypertension, or otherwise in need of the treatment.

The present disclosure also provides uses of crystalline polymorphs of Aprocitentan, Aprocitentan:piperazine, Aprocitentan:methanesulfonic acid, or Aprocitentan:ethanesulfonic acid of the present disclosure, or at least one of the above pharmaceutical compositions, for the manufacture of medicaments for treating e.g. hypertension.

BRIEF DESCRIPTION OF THE DRAWINGS

FIG. 1 shows a characteristic X-ray powder diffraction pattern (XRPD) of Aprocitentan:piperazine Form P1;

FIG. 2 shows a characteristic XRPD of a Aprocitentan:methanesulfonic acid;

FIG. 3 shows a characteristic XRPD of a Aprocitentan:ethanesulfonic acid;

FIG. 4 shows a characteristic XRPD of a Aprocitentan Form T9;

FIG. 5 shows a characteristic XRPD of a Aprocitentan Form T10;

FIG. 6 shows a characteristic XRPD of a Aprocitentan form T12;

FIG. 7 shows a characteristic XRPD of a Aprocitentan, amorphous;

FIG. 8 shows a characteristic XRPD of a Aprocitentan Form T12;

FIG. 9 shows a characteristic XRPD of Aprocitentan:piperazine Form P2;

FIG. 10 shows a characteristic $^{13}$C-NMR spectrum of Aprocitentan Form T12;

FIG. 11 shows a characteristic DSC of Aprocitentan Form T12;

FIG. 12 shows a characteristic TGA of Aprocitentan Form T12;

FIG. 13 shows a characteristic DSC of Aprocitentan Form T10;

FIG. 14 shows a characteristic TGA of Aprocitentan Form T10;

FIG. 15 shows a characteristic FTIR of Aprocitentan piperazine Form P1;

FIG. 16 shows a characteristic DSC of Aprocitentan piperazine Form P1;

FIG. 17 shows a characteristic TGA of Aprocitentan piperazine Form P1;

FIG. 18 shows a characteristic DSC of Aprocitentan piperazine Form P2; and

FIG. 19 shows a characteristic TGA of Aprocitentan piperazine Form P2.

DETAILED DESCRIPTION OF THE DISCLOSURE

The present disclosure encompasses solid state forms of Aprocitentan, including crystalline polymorphs of Aprocitentan, Aprocitentan:piperazine, Aprocitentan:methanesulfonic acid, or Aprocitentan:ethanesulfonic acid, processes for preparation thereof, and pharmaceutical compositions thereof.

Solid state properties of Aprocitentan, Aprocitentan:piperazine, Aprocitentan:methanesulfonic acid, or Aprocitentan:ethanesulfonic acid and crystalline polymorphs thereof can be influenced by controlling the conditions under which Aprocitentan Aprocitentan:piperazine, Aprocitentan:methanesulfonic acid, or Aprocitentan:ethanesulfonic acid and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Aprocitentan, Aprocitentan:piperazine, Aprocitentan:methanesulfonic acid, or Aprocitentan:ethanesulfonic acid described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Aprocitentan, Aprocitentan:piperazine, Aprocitentan:methanesulfonic acid, or Aprocitentan:ethanesulfonic acid. In some embodiments of the disclosure, the described crystalline polymorph of Aprocitentan, Aprocitentan:piperazine, Aprocitentan:methanesulfonic acid, or Aprocitentan:ethanesulfonic acid may contain from about 1% to about 20% (w/w), from about 5% to about 20% (w/w), or from about 5% to about 10% (w/w) of one or more other crystalline polymorph of the same Aprocitentan, Aprocitentan:piperazine, Aprocitentan:methanesulfonic acid, or Aprocitentan:ethanesulfonic acid.

Depending on which other crystalline polymorphs a comparison is made, the crystalline polymorphs of Aprocitentan, Aprocitentan:piperazine, Aprocitentan:methanesulfonic acid, or Aprocitentan:ethanesulfonic acid of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Aprocitentan, Aprocitentan:piperazine, Aprocitentan:methanesulfonic acid, or Aprocitentan:ethanesulfonic acid referred to herein as being characterized by graphical data "as depicted in" or "as substantially depicted in" a Figure will thus be understood to include any crystal forms of Aprocitentan, Aprocitentan:piperazine, Aprocitentan:methanesulfonic acid, or Aprocitentan:ethanesulfonic acid characterized with the graphical data having such small variations, as are well known to the skilled person, in comparison with the Figure.

As used herein, and unless stated otherwise, the term "anhydrous" in relation to crystalline forms of Aprocitentan, Aprocitentan:piperazine, Aprocitentan:methanesulfonic acid, or Aprocitentan:ethanesulfonic acid, relates to a crystalline form of Aprocitentan, Aprocitentan:piperazine, Aprocitentan:methanesulfonic acid, or Aprocitentan:ethanesulfonic acid which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

"Co-Crystal" as used herein is defined as a crystalline material including two or more molecules in the same crystalline lattice and associated by non-ionic and non-covalent bonds. In some embodiments, the co-crystal includes two molecules which are in natural state.

As used herein, crystalline Aprocitentan:piperazine is a distinct molecular species. Crystalline Aprocitentan:piperazine may be a co-crystal of Aprocitentan and piperazine. Alternatively crystalline Aprocitentan: piperazine may be a salt. In any aspect or embodiment of the disclosure herein, a reference to crystalline Aprocitentan:piperazine particularly refers to a co-crystal of Aprocitentan and piperazine.

As used herein, crystalline Aprocitentan:methanesulfonic acid is a distinct molecular species. Crystalline Aprocitentan: methanesulfonic acid may be a co-crystal of Aprocitentan and methanesulfonic acid. Alternatively crystalline Aprocitentan: methanesulfonic acid may be a salt.

As used herein, crystalline Aprocitentan:ethanesulfonic acid is a distinct molecular species. Crystalline Aprocitentan: ethanesulfonic acid may be a co-crystal of Aprocitentan and ethanesulfonic acid. Alternatively crystalline Aprocitentan: ethanesulfonic acid may be a salt.

As used herein, the term "isolated" in reference to crystalline polymorph of Aprocitentan of the present disclosure corresponds to a crystalline polymorph of Aprocitentan that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, λ=1.5418 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure encompasses crystalline Aprocitentan:piperazine designated Form P1. The crystalline Form P1 of Aprocitentan:piperazine may be a co-crystal of Aprocitentan and piperazine. Alternatively, crystalline Form P1 of Aprocitentan:piperazine may be a salt. In any aspect or embodiment of the disclosure herein, a reference to crystalline Aprocitentan:piperazine particularly refers to a co-crystal of Aprocitentan and piperazine.

In embodiments in Form P1 the molar ratio between the active pharmaceutical ingredient (Aprocitentan) and the coformer (piperazine) is about 1:1.5 and 1.5:1, in some embodiments between 1:1.25 and 1.25:1, in other embodiments about 1:1.

Crystalline Form P1 of Aprocitentan:piperazine may be characterized by data selected from one or more of the following: an X-ray powder diffraction pattern substantially as depicted in FIG. 1; an X-ray powder diffraction pattern having peaks at 10.4, 17.2, 21.3, 22.5 and 26.7 degrees 2-theta±0.2 degrees 2-theta; and combinations of these data.

Crystalline Form P1 of Aprocitentan:piperazine may be further characterized by an X-ray powder diffraction pattern having peaks at 10.4, 17.2, 21.3, 22.5 and 26.7 degrees 2-theta±0.2 degrees 2-theta, and also having any one, two, three, four or five additional peaks selected from 8.6, 13.4, 20.9, 23.1 and 25.1 degrees 2-theta±0.2 degrees 2-theta.

Crystalline Form P1 of Aprocitentan:piperazine may alternatively or additionally be characterized by data selected from one or more of the following: a FT-IR as depicted in FIG. 15; a DSC thermogram as depicted in FIG. 16; a TGA thermogram as depicted in FIG. 17. Crystalline Form P1 of Aprocitentan:piperazine shows a melting endothermic peak at about 143.1° C. according to DSC thermogram. Crystalline Form P1 of Aprocitentan; piperazine shows a weight loss of about 1.3%.

In embodiments of the present disclosure, crystalline Form P1 of Aprocitentan:piperazine is isolated.

Crystalline Form P1 of Aprocitentan:piperazine may be an anhydrous or hydrated form. Crystalline Form P1 of Aprocitentan:piperazine may be a hemihydrate.

Crystalline Form P1 of Aprocitentan:piperazine may be characterized by each of the above characteristics alone or by all possible combinations, e.g., an XRPD pattern having peaks at 10.4, 17.2, 21.3, 22.5 and 26.7 degrees 2-theta±0.2 degrees 2-theta; an XRPD pattern as depicted in FIG. 1; and combinations thereof.

The present disclosure further encompasses crystalline Aprocitentan:piperazine designated Form P2. The crystalline Form P2 of Aprocitentan:piperazine may be a co-crystal of Aprocitentan and piperazine. Alternatively, crystalline Form P2 of Aprocitentan:piperazine may be a salt. In any aspect or embodiment of the disclosure herein, a reference to crystalline Aprocitentan:piperazine particularly refers to a co-crystal of Aprocitentan and piperazine.

In embodiments in Form P2 the molar ratio between the active pharmaceutical ingredient (Aprocitentan) and the coformer (piperazine) is between 2.5:1 and 1.7:1, in some embodiments between 2.25:1 and 1.8:1, in other embodiments about 2:1.

Crystalline Form P2 of Aprocitentan:piperazine may be characterized by data selected from one or more of the following: an X-ray powder diffraction pattern substantially as depicted in FIG. 9; an X-ray powder diffraction pattern having peaks at 12.4, 13.2, 16.9, 18.0 and 21.2 degrees 2-theta±0.2 degrees 2-theta; and combinations of these data.

Crystalline Form P2 of Aprocitentan:piperazine may be further characterized by an X-ray powder diffraction pattern having peaks at 12.4, 13.2, 16.9, 18.0 and 21.2 degrees 2-theta±0.2 degrees 2-theta, and also having any one, two, three, four or five additional peaks selected from 19.2, 20.1, 26.6, 28.3 and 31.0 degrees 2-theta±0.2 degrees 2-theta.

Crystalline Form P2 of Aprocitentan:piperazine may alternatively or additionally be characterized by data selected from one or more of the following: a DSC thermogram as depicted in FIG. 18; a TGA thermogram as depicted in FIG. 19; Crystalline Form P2 of Aprocitentan:piperazine shows a melting endothermic peak at about 154.5° C. according to DSC thermogram. Further, crystalline Form P2 of Aprocitentan:piperazine shows a weight loss of about 0.7% up to 130° C.

In embodiments of the present disclosure, crystalline Form P2 of Aprocitentan:piperazine is isolated.

Crystalline Form P2 of Aprocitentan:piperazine may be an anhydrous or hydrated form.

Crystalline Form P2 of Aprocitentan:piperazine may be characterized by each of the above characteristics alone or by all possible combinations, e.g., an XRPD pattern having peaks at 12.4, 13.2, 16.9, 18.0 and 21.2 degrees 2-theta±0.2 degrees 2-theta; an XRPD pattern as depicted in FIG. 9; and combinations thereof.

The present disclosure further encompasses crystalline Aprocitentan:methanesulfonic acid. The crystalline Aprocitentan:methanesulfonic acid may be a co-crystal of Aprocitentan and methanesulfonic acid. Alternatively, crystalline Aprocitentan:methanesulfonic acid may be a salt.

Crystalline Form of Aprocitentan:methanesulfonic acid may be characterized by data selected from one or more of the following: an X-ray powder diffraction pattern substantially as depicted in FIG. 2; an X-ray powder diffraction pattern having peaks at 9.2, 12.1, 13.7, 16.5 and 21.2 degrees 2-theta±0.2 degrees 2-theta; and combinations of these data.

Crystalline Form of Aprocitentan:methanesulfonic acid may be further characterized by an X-ray powder diffraction pattern having peaks at 9.2, 12.1, 13.7, 16.5 and 21.2 degrees 2-theta±0.2 degrees 2-theta, and also having any one, two, three, four or five additional peaks selected from 17.6, 19.2, 23.0, 24.7 and 28.0 degrees 2-theta±0.2 degrees 2-theta.

In embodiments of the present disclosure, crystalline Form of Aprocitentan:methanesulfonic acid is isolated.

Crystalline Form of Aprocitentan:methanesulfonic acid may be an anhydrous form.

Crystalline Form of Aprocitentan:methanesulfonic acid may be characterized by each of the above characteristics alone or by all possible combinations, e.g., an XRPD pattern having peaks at 9.2, 12.1, 13.7, 16.5 and 21.2 degrees 2-theta±0.2 degrees 2-theta; an XRPD pattern as depicted in FIG. 2; and combinations thereof.

The present disclosure further encompasses crystalline Aprocitentan:ethanesulfonic acid. The crystalline Aprocitentan:ethanesulfonic acid may be a co-crystal of Aprocitentan and ethanesulfonic acid. Alternatively, crystalline Aprocitentan:ethanesulfonic acid may be a salt.

Crystalline Form of Aprocitentan:ethanesulfonic acid may be characterized by data selected from one or more of the following: an X-ray powder diffraction pattern substantially as depicted in FIG. 3; an X-ray powder diffraction pattern having peaks at 10.9, 12.7, 18.1, 19.3 and 21.0 degrees 2-theta±0.2 degrees 2-theta; and combinations of these data.

Crystalline Form of Aprocitentan:ethanesulfonic acid may be further characterized by an X-ray powder diffraction pattern having peaks at 10.9, 12.7, 18.1, 19.3 and 21.0 degrees 2-theta±0.2 degrees 2-theta, and also having any one, two, three, four or five additional peaks selected from 14.1, 14.9, 23.0, 25.2 and 25.9 theta±0.2 degrees 2-theta.

In embodiments of the present disclosure, crystalline Form of Aprocitentan:ethanesulfonic acid is isolated.

Crystalline Form of Aprocitentan:ethanesulfonic acid may be an anhydrous form.

Crystalline Form of Aprocitentan:ethanesulfonic acid may be characterized by each of the above characteristics alone or by all possible combinations, e.g., an XRPD pattern having peaks at 10.9, 12.7, 18.1, 19.3 and 21.0 degrees 2-theta±0.2 degrees 2-theta; an XRPD pattern as depicted in FIG. 3; and combinations thereof.

The present disclosure further includes a crystalline polymorph of Aprocitentan, designated Form T9. The crystalline Form T9 of Aprocitentan may be characterized by data selected from one or more of the following: an X-ray powder diffraction pattern substantially as depicted in FIG. 4; an X-ray powder diffraction pattern having peaks at 12.6, 16.3, 20.8, 24.1 and 26.7 degrees 2-theta±0.2 degrees 2-theta; and combinations of these data.

Crystalline Form T9 of Aprocitentan may be further characterized by an X-ray powder diffraction pattern having peaks at 12.6, 16.3, 20.8, 24.1 and 26.7 degrees 2-theta±0.2 degrees 2-theta, and also having any one, two, three, four or five additional peaks selected from 10.4, 18.9, 22.3, 26.0 and 28.1 degrees 2-theta±0.2 degrees 2-theta.

In one embodiment of the present disclosure, crystalline Form T9 of Aprocitentan is isolated.

Crystalline Form T9 of Aprocitentan may be methyl acetate solvate form.

Crystalline Form T9 of Aprocitentan may be characterized by each of the above characteristics alone/or by all possible combinations, e.g., an XRPD pattern having peaks at 12.6, 16.3, 20.8, 24.1 and 26.7 degrees 2-theta±0.2 degrees 2-theta; an XRPD pattern as depicted in FIG. 4, and combinations thereof.

The present disclosure further includes a crystalline polymorph of Aprocitentan, designated Form T10. The crystalline Form T10 of Aprocitentan may be characterized by data selected from one or more of the following: an X-ray powder diffraction pattern substantially as depicted in FIG. 5; an X-ray powder diffraction pattern having peaks at 13.3, 14.9, 16.2, 22.2 and 27.9 degrees 2-theta±0.2 degrees 2-theta; and combinations of these data.

Crystalline Form T10 of Aprocitentan may be further characterized by an X-ray powder diffraction pattern having peaks at 13.3, 14.9, 16.2, 22.2 and 27.9 degrees 2-theta±0.2 degrees 2-theta, and also having any one, two, three, four or five additional peaks selected from 18.0, 19.2, 20.8, 23.8 and 26.3 degrees 2-theta±0.2 degrees 2-theta.

Crystalline Form T10 of Aprocitentan may alternatively or additionally be characterized by data selected from one or more of the following: a DSC thermogram as depicted in FIG. 13; a TGA thermogram as depicted in FIG. 14. Crystalline Form T10 of Aprocitentan shows a weight loss of about 7.3% up to 125° C. indicating that Form T10 is solvated form.

In one embodiment of the present disclosure, crystalline Form T10 of Aprocitentan is isolated.

Crystalline Form T10 of Aprocitentan may be ethoxy-ethane solvate form.

Crystalline Form T10 of Aprocitentan may be characterized by each of the above characteristics alone/or by all possible combinations, e.g., an XRPD pattern having peaks at 13.3, 14.9, 16.2, 22.2 and 27.9 degrees 2-theta±0.2 degrees 2-theta; an XRPD pattern as depicted in FIG. 5, and combinations thereof.

The present disclosure further includes a crystalline polymorph of Aprocitentan, designated Form T12. The crystalline Form T12 of Aprocitentan may be characterized by data selected from one or more of the following: an X-ray powder diffraction pattern substantially as depicted in FIG. 6 or 8; an X-ray powder diffraction pattern having peaks at 10.1, 13.3, 24.5, 26.7 and 28.5 degrees 2-theta±0.2 degrees 2-theta; and combinations of these data.

Crystalline Form T12 of Aprocitentan may be further characterized by an X-ray powder diffraction pattern having peaks at 10.1, 13.3, 24.5, 26.7 and 28.5 degrees 2-theta±0.2 degrees 2-theta, and also having any one, two, three, four or five additional peaks selected from 16.4, 19.4, 22.7, 26.2 and 28.1 degrees 2-theta±0.2 degrees 2-theta.

Crystalline Form T12 of Aprocitentan may alternatively or additionally be characterized by data selected from one or more of the following: a solid state $^{13}$C-NMR spectrum with peaks at 165.9, 162.0, 131.6, 128.9 and 103.7 ppm±0.2 ppm; or by a solid state $^{13}$C-NMR spectrum having the following chemical shift absolute differences from a peak at 65.3 ppm±2 ppm of 100.6, 96.7, 66.3, 63.6 and 38.4 ppm±0.1 ppm; or by a solid state $^{13}$C NMR spectrum having chemical shift difference from a peak at 165.9 ppm±1 ppm of 100.6 ppm±0.1 ppm; or by a solid state $^{13}$C-NMR spectrum substantially as depicted in FIG. 10; or by combinations of these data.

Crystalline Form T12 of Aprocitentan may alternatively or additionally be characterized by data selected from one or more of the following: by a DSC thermogram as depicted in FIG. 11; or by a TGA thermogram as depicted in FIG. 12, or by combinations of these data. Crystalline Form T12 of Aprocitentan shows a melting endothermic peak at about 112.3° C. Crystalline Form T12 of Aprocitentan shows a weight loss of about 0.3% up to 130° C.

In one embodiment of the present disclosure, crystalline Form T12 of Aprocitentan is isolated.

Crystalline Form T12 of Aprocitentan may be anhydrous form.

Crystalline Form T12 of Aprocitentan may be characterized by each of the above characteristics alone/or by all possible combinations, e.g., an XRPD pattern having peaks at 10.1, 13.3, 24.5, 26.7 and 28.5 degrees 2-theta±0.2 degrees 2-theta; an XRPD pattern as depicted in FIG. 6 or 8, and combinations thereof.

The above crystalline polymorphs can be used to prepare other crystalline polymorphs of Aprocitentan, Aprocitentan salts and their solid state forms or co-crystals of Aprocitentan and their solid state forms.

The present disclosure encompasses a process for preparing other solid state forms of Aprocitentan, Aprocitentan salts and their solid state forms or co-crystals of Aprocitentan and their solid state forms.

The present disclosure encompasses a process for preparing other solid state forms of Aprocitentan, Aprocitentan salts and their solid state forms or co-crystals of Aprocitentan and their solid state forms. The process comprises preparing any one of the solid state forms of Aprocitentan, Aprocitentan:piperazine, Aprocitentan:methanesulfonic acid, or Aprocitentan:ethanesulfonic of the present disclosure by the processes of the present disclosure, and converting it to another form of Aprocitentan, Aprocitentan salts or co-crystals of Aprocitentan. The conversion can be done, for example, by a process comprising reacting one of the above described forms of Aprocitentan with an appropriate acid, to obtain the corresponding salt. Alternatively, the conversion can be done by salt switching, i.e., reacting any one of the forms of the Aprocitentan salts of the present disclosure with an acid having a pKa which is lower than that of the acid of the original salt.

The present disclosure provides the above described crystalline polymorphs of Aprocitentan, Aprocitentan:piperazine, Aprocitentan:methanesulfonic acid, or Aprocitentan:ethanesulfonic acid for use in the preparation of pharmaceutical compositions comprising Aprocitentan and/or crystalline polymorphs thereof.

The present disclosure also encompasses the use of crystalline polymorphs of Aprocitentan, Aprocitentan:piperazine, Aprocitentan:methanesulfonic acid, or Aprocitentan:ethanesulfonic acid of the present disclosure for the preparation of pharmaceutical compositions of crystalline polymorph Aprocitentan and/or crystalline polymorphs thereof.

The present disclosure includes processes for preparing the above mentioned pharmaceutical compositions. The processes include combining any one or a combination of the crystalline polymorphs of Aprocitentan, Aprocitentan:piperazine, Aprocitentan:methanesulfonic acid, or Aprocitentan:ethanesulfonic acid of the present disclosure with at least one pharmaceutically acceptable excipient.

Pharmaceutical combinations or formulations of the present disclosure contain any one or a combination of the solid state forms of Aprocitentan, Aprocitentan:piperazine, Aprocitentan:methanesulfonic acid, or Aprocitentan:ethanesulfonic acid of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Aprocitentan, Aprocitentan:piperazine, Aprocitentan:methanesulfonic acid, or Aprocitentan:ethanesulfonic acid and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Aprocitentan, Aprocitentan:piperazine, Aprocitentan:methanesulfonic acid, or Aprocitentan:ethanesulfonic acid can be administered. Aprocitentan, Aprocitentan:piperazine, Aprocitentan:methanesulfonic acid, or Aprocitentan:ethanesulfonic acid may be formulated for administration to a mammal, in embodiments to a human, by injection. Aprocitentan, Aprocitentan:piperazine, Aprocitentan:methanesulfonic acid, or Aprocitentan:ethanesulfonic acid can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Aprocitentan, Aprocitentan:piperazine, Aprocitentan:methanesulfonic acid, or Aprocitentan:ethanesulfonic acid and the pharmaceutical compositions and/or formulations of Aprocitentan, Aprocitentan:piperazine, Aprocitentan:methanesulfonic acid, or Aprocitentan:ethanesulfonic acid of the present disclosure can be used as medicaments, in embodiments in the treatment of hypertension.

The present disclosure also provides methods of treating hypertension by administering a therapeutically effective amount of any one or a combination of the crystalline polymorphs of Aprocitentan, Aprocitentan:piperazine, Aprocitentan:methanesulfonic acid, or Aprocitentan:ethanesulfonic acid of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

A sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Angstrom), X'Celerator (2.022° 2θ) detector. Scanning parameters: angle range: 3-40 deg., step size 0.0167, time per step 37 s, continuous scan. The described peak positions were determined without using silicon powder as an internal standard in an admixture with the sample measured.

DSC Analysis

Equipment
TA Instruments Discovery DSC
Scanning parameters
Heating range: 25-300° C.
Heating rate: 10 C°/min
Sample placed in hermetically closed aluminum pan with one hole on the crucible.
Purging with 50 ml/min $N_2$ flow.

TGA Analysis

Equipment
TA Instruments Discovery TGA
Scanning parameters
Heating range: 25-300° C.
Heating rate: 10 C°/min
Sample placed in hermetically closed aluminum pan with one hole on the crucible.
Purging with 50 ml/min $N_2$ flow Solid State $^{13}$C-NMR Analysis Solid state NMR spectra was measured at 11.7 T using a Bruker Avance III HD 500 US/WB NMR spectrometer (Karlsruhe, Germany, 2013). The $^{13}$C CP/MAS NMR spectra employing cross-polarization were acquired using the standard pulse scheme at spinning frequency of 11 kHz. The recycle delay was 8 s and the cross-polarization contact time was 2 ms. The strength of spin-locking fields B1($^{13}$C) expressed in frequency units $\omega 1/2\eta = \gamma B1$ was 64 kHz.

The $^{13}$C NMR scale was referenced to α-glycine (176.03 ppm). Frictional heating of the spinning samples was offset by active cooling, and the temperature calibration was performed with Pb(NO$_3$)$_2$. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height $\Delta v\frac{1}{2}$ was less than 3.5 Hz at 250 ms of acquisition time).

Solid State FT-IR Analysis

FTIR spectra were recorded on Instrument: Nicolet 6700 FT-IR spectrometer. Sample was prepared as KBr pellet. Empty sample compartment was used for background spectrum acquisition. The spectra were scanned between: 4000-400 cm-1. All the spectra were measured in 16 scans, resolution: 4.0 cm$^{-1}$.

EXAMPLES

Preparation of Starting Materials

Aprocitentan can be prepared according to methods known from the literature, for example as described in U.S. Pat. No. 6,638,937 or U.S. Pat. No. 8,324,232.

Example 1: Preparation of Aprocitentan:Piperazine Form P1

Aprocitentan (1.20 grams) was dissolved in methyl acetate (24 mL) at 53° C. The solution was cooled to 35° C. and to the stirred solution piperazine (189 mg, 1 eq.) was added. The suspension was stirred for another 30 minutes. The solid was isolated by vacuum filtration and dried in air for 20 minutes. The obtained solid was further dried in a vacuum drier at 70° C. for 4 hours. The obtained solid was analyzed by XRPD. Crystalline Aprocitentan:piperazine was obtained (yield: 89%). XRPD pattern is given in FIG. 1.

Example 2: Preparation of Aprocitentan:Methanesulfonic Acid

Aprocitentan (600 mg) was dissolved in methyl acetate (10 mL) at 52° C. To the stirred solution methanesulfonic acid (71.3 µL, 1 eq.) was added. The obtained solution was cooled to 0° C. in an ice water bath, precipitation started around 35° C. The obtained solid was isolated by vacuum filtration and dried in air for 20 minutes. The obtained solid was analyzed by XRPD. Crystalline Aprocitentan:methanesulfonic acid was obtained (yield: 69%). XRPD pattern is given in FIG. 2.

Example 3: Preparation of Aprocitentan:Ethanesulfonic Acid

Aprocitentan (600 mg) was dissolved in methyl acetate (10 mL) at 52° C. To the stirred solution ethanesulfonic acid (89.6 µL, 1 eq.) was added. The obtained solution was cooled to 0° C. in an ice water bath, precipitation started around 40° C. The obtained solid was isolated by vacuum filtration and dried in air for 20 minutes. The obtained solid was analyzed by XRPD. Crystalline Aprocitentan:ethanesulfonic acid was obtained (yield: 79%). XRPD pattern is given in FIG. 3.

Example 4: Preparation of Aprocitentan, Form T9

Aprocitentan (300 mg) was dissolved in methyl acetate (7 mL) at 56° C. The solution was stirred for 10 min and then cooled to 0° C. in an ice water bath and stirred for another 2 hours. The solution was left stirring for 16 hours at 25° C. The obtained solid was isolated by vacuum filtration and dried in air for 20 minutes. The obtained solid was analyzed by XRPD. Aprocitentan form T9, methyl acetate solvate was obtained. XRPD pattern is given in FIG. 4.

Example 5: Preparation of Aprocitentan, Form T10

Amorphous Aprocitentan (50 mg) prepared according to Example 8 (below), was charged into a glass vial with ethoxyethane (0.5 mL). The suspension was stirred for 4 days at 25° C. The obtained solid was isolated by vacuum filtration and dried in air for 20 min. The obtained solid was analyzed by XRPD. Aprocitentan form T10 was obtained. XRPD pattern is given in FIG. 5.

Example 6: Preparation of Aprocitentan, Form T10

Aprocitentan (300 mg) was dissolved in acetone (6 mL) at 25° C. To the solution ethoxyethane (20 mL) was added dropwise. The resulting solution was cooled to 5° C. in an ice water bath and stirred for 2 hours at 5° C. The resulting suspension was left stirring for 16 hours at 25° C. Solid was isolated by vacuum filtration and dried in air for 20 minutes. The obtained solid was analyzed by XRPD. Aprocitentan form T10 was obtained.

Example 7: Preparation of Aprocitentan, Form T12

Aprocitentan form T10 (200 mg) was dried in a vacuum dryer at 70° C. for 4 hours. The obtained solid was analyzed by XRPD. Aprocitentan form T12 was obtained. XRPD pattern is given in FIG. 6.

Example 8: Preparation of Amorphous Aprocitentan

Aprocitentan (2.0 grams) was dissolved in acetone (60 mL) at 50° C. The solution was filtered and solvent was removed by vacuum evaporation (50° C., 10 mbar). The obtained dry solid was analyzed by XRPD. Amorphous Aprocitentan was obtained. XRPD pattern is given in FIG. 7.

Example 9: Preparation of Aprocitentan, Form T12

Aprocitentan Form T10 (1.0 g) was vacuum dried at 80° C. for 10 h. Solid was analyzed by XRPD, Aprocitentan anhydrous form T12 was obtained. XRPD pattern is given in FIG. 8.

Example 10: Preparation of Aprocitentan:Piperazine Form P2

Aprocitentan (1.00 g) was charged into a round-bottom three-necked flask with methanol (35 mL). The mixture was heated to 60° C. and stirred until the solid completely dissolved. To the stirred solution piperazine (158 mg, 1 eq.) was added. The resulting solution was cooled to 25° C. and stirred for 30 min. The obtained solid was isolated by vacuum filtration and analyzed by XRPD. Crystalline Aprocitentan—piperazine Form P2 was obtained. XRPD pattern is given in FIG. 9.

The invention claimed is:
1. A crystalline Form T12 of Aprocitentan, which is characterized by data selected from one or more of the following:
   i) an XRPD pattern having peaks at 10.1, 13.3, 24.5, 26.7 and 28.5 degrees-2-theta±0.2 degrees 2-theta;
   ii) an XRPD pattern as depicted in FIG. 6 or FIG. 8;
   iii) a solid state $^{13}$C-NMR spectrum with peaks at 165.9, 162.0, 131.6, 128.9 and 103.7 ppm±0.2 ppm;
   iv) a solid state $^{13}$C-NMR spectrum following chemical shift absolute differences from a peak at 65.3 ppm±2 ppm of 100.6, 96.7, 66.3, 63.6 and 38.4 ppm±0.1 ppm;
   v) a solid state $^{13}$C NMR spectrum having chemical shift difference from a peak at 165.9 ppm±1 ppm of 100.6 ppm±0.1 ppm;

vi) a solid state $^{13}$C-NMR spectrum substantially as depicted in FIG. 10; or combinations of (i)-(vi).

2. The crystalline form of Aprocitentan according to claim 1, which is further characterized by an XRPD pattern having peaks at 10.1, 13.3, 24.5, 26.7 and 28.5 degrees-2-theta±0.2 degrees 2-theta, and also having one, two, three, four or five additional peaks selected from 16.4, 19.4, 22.7, 26.2 and 28.1 degrees-2-theta±0.2 degrees 2-theta.

3. A crystalline Form T10 of Aprocitentan, which is characterized by data selected from one or more of the following:
- i) an XRPD pattern having peaks at 13.3, 14.9, 16.2, 22.2 and 27.9 degrees-2-theta±0.2 degrees 2-theta;
- ii) an XRPD pattern as depicted in FIG. 5; or
    combinations of (i) and (ii).

4. The crystalline form of Aprocitentan according to claim 3, which is further characterized by an XRPD pattern having peaks at 13.3, 14.9, 16.2, 22.2 and 27.92 degrees-2-theta±0.2 degrees 2-theta, and also having one, two, three, four or five additional peaks selected from 18.0, 19.2, 20.8, 23.8 and 26.3 degrees-2-theta±0.2 degrees 2-theta.

5. A crystalline product of Aprocitentan: piperazine designated Form P1, which is characterized by data selected from one or more of the following:
- i) an XRPD pattern having peaks at 10.4, 17.2, 21.3, 22.5 and 26.7 degrees 2-theta±0.2 degrees 2-theta;
- ii) an XRPD pattern as depicted in FIG. 1;
- iii) an FT-IR as depicted in FIG. 15;
- iv) or combinations of (i)-(iii).

6. The crystalline product of Aprocitentan: piperazine according to claim 5, which is a co-crystal.

7. The crystalline product of Aprocitentan: piperazine according to claim 5 designated Form P1, which is characterized by an XRPD pattern having peaks at 10.4, 17.2, 21.3, 22.5 and 26.7 degrees 2-theta±0.2 degrees 2-theta, and also having one, two, three, four or five additional peaks selected from 8.6, 13.4, 20.9, 23.1 and 25.1 degrees 2-theta±0.2 degrees 2-theta.

8. The crystalline product of Aprocitentan: piperazine according to claim 5 designated Form P1, wherein the ratio between Aprocitentan and piperazine is between 1:1.5 and 1.5:1 or between 1:1.25 and 1.25:1, or about 1:1.

9. A crystalline product of Aprocitentan: piperazine designated Form P2, which is characterized by data selected from one or more of the following:
- i) an XRPD pattern having peaks at 12.4, 13.2, 16.9, 18.0 and 21.2 degrees 2-theta±0.2 degrees 2-theta;
- ii) an XRPD pattern as depicted in FIG. 9; or
    comnbinations of (i) and (ii).

10. The crystalline product of Aprocitentan: piperazine according to claim 9 designated Form P2, which is characterized by an XRPD pattern having peaks at 12.4, 13.2, 16.9, 18.0 and 21.2 degrees 2-theta±0.2 degrees 2-theta, and also having one, two, three, four or five additional peaks selected from 19.2, 20.1, 26.6, 28.3 and 31.0 degrees 2-theta±0.2 degrees 2-theta.

11. The crystalline product according to claim 9 designated Form P2, wherein the ratio between Aprocitentan and piperazine is between 2.5:1 and 1.7:1, or between 2.25:1 and 1.8:1, or about 2:1.

12. A pharmaceutical composition comprising the crystalline form according to claim 1 and at least one pharmaceutically acceptable excipient.

13. A pharmaceutical formulation comprising the crystalline form according to claim 3 and at least one pharmaceutically acceptable excipient.

14. A pharmaceutical composition comprising the crystalline product according to claim 5 and at least one pharmaceutically acceptable excipient.

15. A pharmaceutical formulation comprising the crystalline product according to claim 10 and at least one pharmaceutically acceptable excipient.

\* \* \* \* \*